(12) United States Patent
Chow et al.

(10) Patent No.: US 7,932,430 B2
(45) Date of Patent: Apr. 26, 2011

(54) DEVELOPMENT OF A SIMPLE ANIMAL MODEL FOR INFECTION BY VIRUSES AND OTHER OBLIGATE INTRACELLULAR PARASITES

(75) Inventors: Marie Chow, Little Rock, AR (US); Courtney Wilkins, Little Rock, AR (US); Khaled Machaca, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 321 days.

(21) Appl. No.: 11/982,162

(22) Filed: Nov. 1, 2007

(65) Prior Publication Data

US 2009/0257954 A1 Oct. 15, 2009

(51) Int. Cl.
*A61K 39/12* (2006.01)
(52) U.S. Cl. .......................... 800/13; 800/21; 424/204.1
(58) Field of Classification Search .................. None
See application file for complete search history.

(56) References Cited

OTHER PUBLICATIONS

Shaham, Shai, PNAS USA, Mar. 14, 2006, 103(11):3955-3956.*
Epstein, H.S. and D.C. Shakes eds. 1995. *C. elegans*. Modem Biology Analysis of an Organism. Methods in Cell Biology. Academic Press. vol. 48.
Garsin et al. 2001. A simple model for identifying Gram positive virulence factors. Proceedings in National Academy of Science. 98:10892-97.
Kim et al. 2002. A conserved p38 Map kinase pathway in *Caenorhabditis elegans* innate immunity. Science. 297:623-26.
Labrousse et al. 2000. *C. elegans* is a model host for *Salmonella typhimurium*. Current Biology. 10:1543-45.
Mahajan-Miklos et al. 1999. Molecular mechanisms of bacteria virulence elucidated using a *P. aeruginosa—C. elegans* pathogenesis model. Cell 96:47-56.
Pujol et al. 2001. A reverse genetic analysis of components of the Toll signaling pathway in *C. elegans*. Current Biology. 11:809-21.
Tan et al. 1999. *P. aeruginosa* killing *C. elegans* used to identify *P. aeruginosa* virulence factors. Proceedings in National Academy of Science. 96:2408-13.

* cited by examiner

*Primary Examiner* — Stacy B Chen
(74) *Attorney, Agent, or Firm* — Angela Foster, Esq.

(57) ABSTRACT

The present invention provides methods for studying pathogenesis of mammalian viruses. In particular, the present invention provides a nonhuman animal model system for studying disease mechanisms wherein the nonhuman animal model is infected with an animal virus. In a preferred embodiment the animal model is *C. elegans* and the animal virus is vesicular stomatitis virus (VSV).

6 Claims, 7 Drawing Sheets

Figure 1:
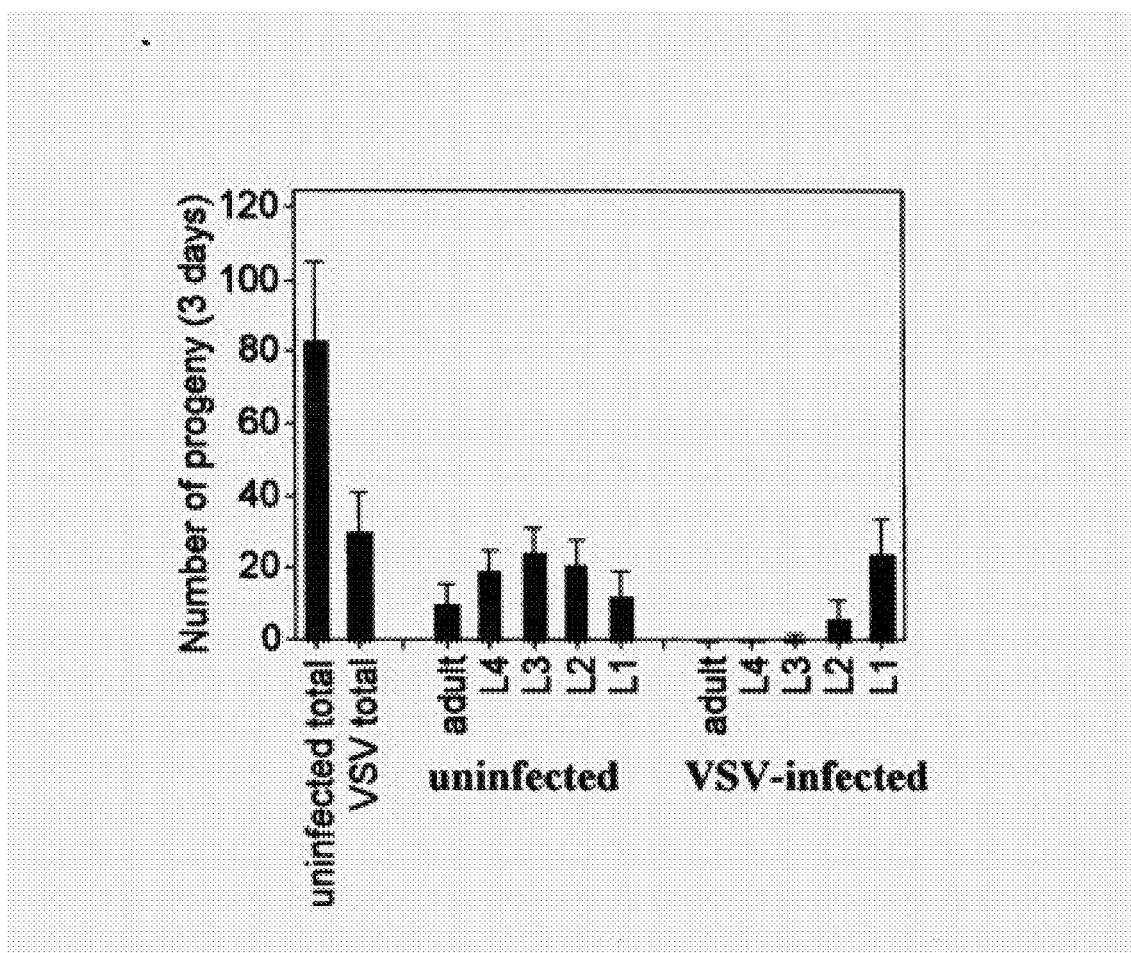

VSV infects wild type *C. elegans* cells in culture

US 7,932,430 B2

DEVELOPMENT OF A SIMPLE ANIMAL MODEL FOR INFECTION BY VIRUSES AND OTHER OBLIGATE INTRACELLULAR PARASITES

1. RELATED APPLICATIONS

This application claims the benefit of U.S. Provisional Application No. 60/435,806, filed on Dec. 22, 2002 and U.S. Nonprovisional application Ser. No. 10/746,672 filed on Dec. 22, 2003 now U.S. Pat. No. 7,326,528.

2. FIELD OF INVENTION

The present invention relates to animal models and methods for studying pathogenesis of mammalian viruses. More specifically, the present invention provides a disease model of Vesicular Stomatitis Virus infection with *C. elegans* and methods for studying disease phenomenon.

3. BACKGROUND OF THE INVENTION

Effective design of antiviral therapeutics, diagnostic devices and vaccines requires understanding viral mechanism of disease pathogenesis. Presently, viral replication and disease mechanisms are studied either in cell culture or vertebrate hosts such as rodents (mice, rats, guinea pigs) or nonhuman primates. However, cell culture systems do not provide proper models for studying disease mechanisms involving physiological responses of multicellular origins such as the inflammatory process or innate immune responses or viral induced immunopathologies. Viral pathogenic studies in intact vertebrate hosts such as mice present difficulties due to many factors including the number of animals required for statistically significant results, long experimental duration times and high expense.

Disease development upon virus infection is highly dependent on the genetics and physiology of the host. Viruses are obligate intracellular parasites and depend on various components of the host machinery for nearly all aspects of their life cycle, including replication, gene expression and cell-to-cell spread. As viruses manipulate the host cellular and systemic physiology, host responses lead either to disease development or recovery. For mammalian animal viruses, previous studies of host factors conferring susceptibility or resistance to viral infection have been limited to in vitro host models using infected cells or tissue culture or in vivo models involving experimental infection of primate or small animal mammalian hosts. Both in vitro and in vivo models of viral infection have major disadvantages. Mammalian models, namely mouse or primates, are costly and technically demanding. Sample sizes are often limited. In addition, genetic manipulation of the host genome is technically difficult and often requires long generation times. In vitro tissues and/or cell culture addresses many of these problems but lack the ability to conduct studies on disease aspects that depend on the physiological responses of multiple organs or cellular systems. Therefore, a simple animal model system capable of elucidating viral disease mechanisms of mammalian systems is desired.

The nematode *Caenorhabditis elegans* (*C. elegans*) is an attractive model system for studying viral disease for a number of technical and scientific reasons. In particular the complete genome has been sequenced and a well characterized genetic map and a collection of mutants are available. Moreover, the *C. elegans*' fast generation time and simple an inexpensive maintenance makes it relatively easy to obtain large sample sizes for experimental studies. Previous studies with *C. elegans* as models for bacterial pathogenesis demonstrated a disease phenotype in the nematode upon exposure to certain strains of *Pseudomonas*, a facultative intracellular bacterial pathogen. (Mahajan-Miklos et al., 1999 *Cell* 96: 47-56 and Tan et al., 1999 *Proc. Natl. Acad Sci. USA* 96: 2408-2413). Disease occurrence was dependent on several bacterial genes previously shown to be necessary for virulence in other infection models. In addition, several new virulence-associated genes were identified. These initial studies were extended to show that other facultative intracellular bacterial pathogens, including *Salmonella* (Labrousse et al., 2000 *Current Biology* 10: 1543-1545) and a variety of gram-positive pathogens (Garsin et al., 2000 *Proc. Natl. Acad. Sci. USA* 98: 10872-10877) can also induce disease in *C. elegans*. Other studies have focused on host defense mechanisms involved in controlling bacterial infections (Pujol el al., 2001 *Current Biology* 11: 809-821). Random mutagenesis screens have identified components of the mitogen-activated protein kinases (MAPK) signaling pathway as being influential in host susceptibility to bacterial infection in the nematode (Kim et al., 2002 *Science* 297: 623-626). Yet, no studies have demonstrated disease susceptibility of *C. elegans* by animal viruses not known to infect *C. elegans* until the present invention. Accordingly, the present invention provides a simple model system that can be used to study disease pathogenesis of mammalian viruses.

4. SUMMARRY OF THE INVENTION

The present invention relates to the inventors' unexpected ability to demonstrate that vesicular stomatitis virus (VSV) can cause disease in *C. elegans*, an invertebrate which is not known to be infected by VSV or other vertebrate animal viruses. VSV is an enveloped virus with a negative-sense RNA genome that must be transcribed by a virus-encoded RNA-dependent RNA polymerase to replicate the viral RNA genome and to produce mRNAs which are used in synthesis of viral proteins. VSV lethally infects vertebrate animal cells in in vitro culture and viral infection of whole animal such as mice, causes disease.

Therefore, the present invention provides an animal model for studying disease mechanisms comprising *C. elegans* infected with an animal virus. In a preferred embodiment, *C. elegans* is infected with VSV.

The *C. elegans* can be wild-type, mutant or transgenic. Moreover, the transgenic *C. elegans* may comprise a reporter gene such as but not limited to luciferease or the green fluorescent protein wherein the expression of the reporter protein is dependent on the presence of viral gene expression or viral infection.

Potential therapeutics that target symptom pathways may interfere with the development of diseases but do not significantly effect viral replication. Therefore, the present invention provides an infection model system for screening agents that interact with disease development. In one embodiment of the present method, *C. elegans* infected with an animal virus is combined with an agent and the effect of the agent on a phenomenon associated with viral disease mechanisms is determined.

In another embodiment, the present invention provides a method for identifying host genes that are involved in disease development. In still another embodiment, the present invention provides a method for studying disease conditions comprising infecting *C. elegans* with VSV and detecting an abnormal phenotype in the infected *C. elegans* which is not observed in healthy uninfected *C. elegans*. These phenotypes which may vary with the disease conditions, include but are not limited to decreased numbers of progeny, altered larval development, muscle abnormalities leading to uncoordinated movement or egg-laying defects, altered lifespan of the adult C. elegans and death.

5. DESCRIPTION OF THE FIGURES

FIG. 1 demonstrates that vesicular stomatits virus (VSV) decreases C. elegans population size and skews larval development. Individual L3 larvae were cultured in liquid media in the presence or absence of $10^6$ PFU/ml VSV fluorescent protein (VSV-GFP) recombinant virus. After 3 days at 25° C., total progeny and number per developmental stage were counted.

Figure 2:
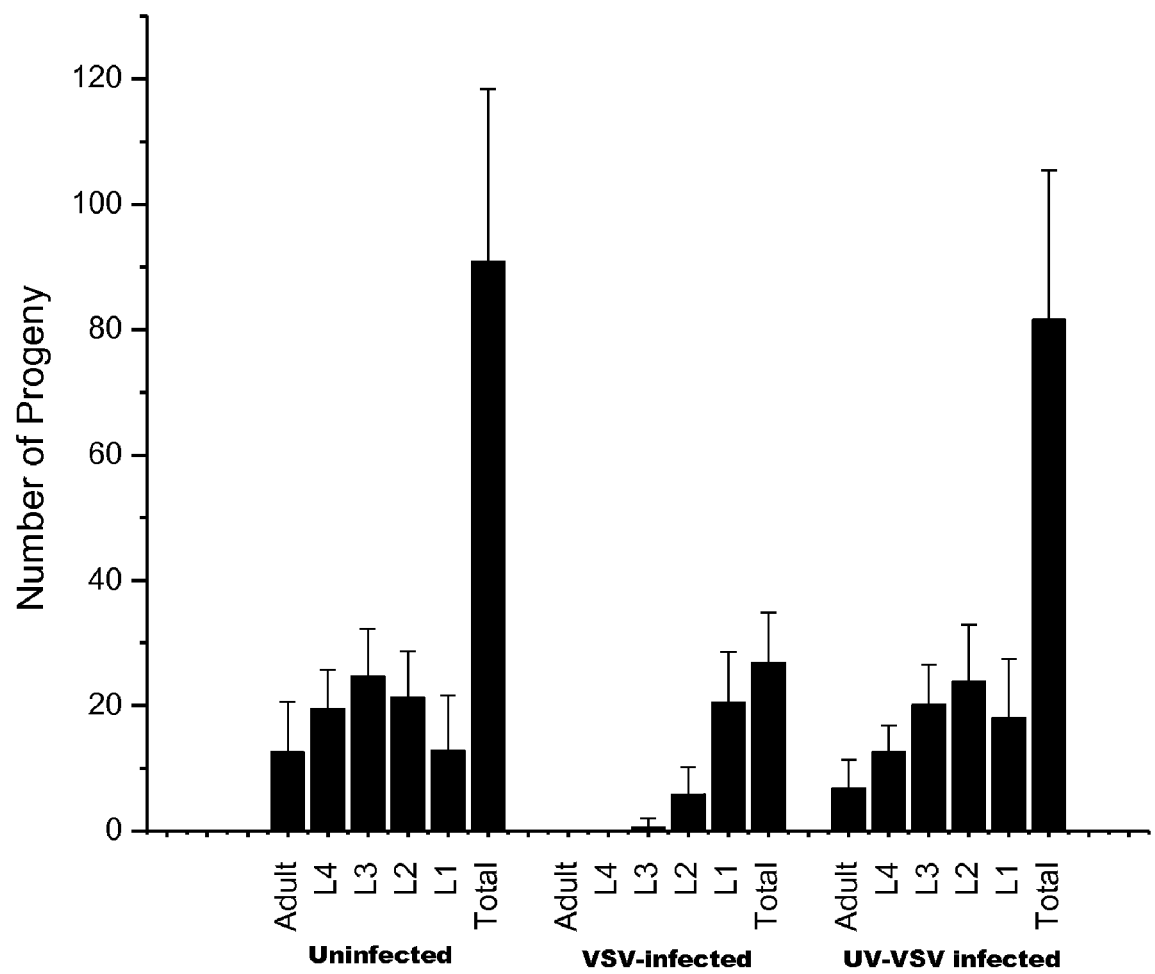

FIG. 2 demonstrates that infectious VSV is responsible for the decrease in population size in C. elegans. Individual L3 larvae were cultured in liquid media in the absence of virus, in the presence of $10^6$ PFU/ml VSV fluorescent protein (VSV-GFP) recombinant virus or in the presence of the equivalent amount of UV-inactivated VSV-GFP. After 3 days at 25° C., total progeny and number per developmental stage were counted.

Figure 3:
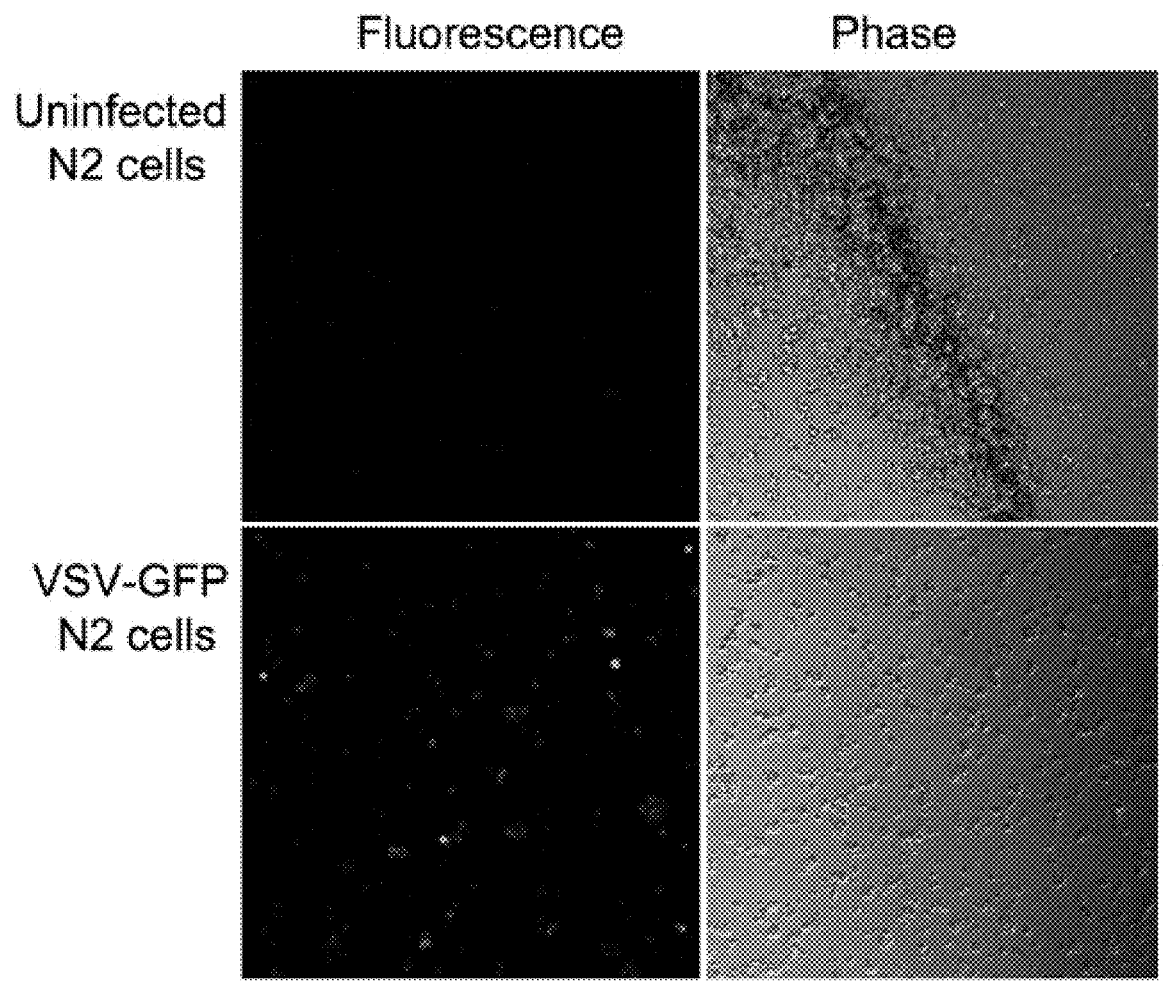

FIG. 3 demonstrates fluorescent and phase-contrast images of cells isolated from C. elegans embryos that were infected with vesicular stomatitis virus-green fluorescent protein (VSV-GFP) recombinant virus. Cells were incubated with the recombinant virus for 12 hours at 25° C. at a multiplicity of 10 infectious units per cell. At 48 hour post-infection, the cells were examined by fluorescent microscopy for GFP expression.

Figure 4:
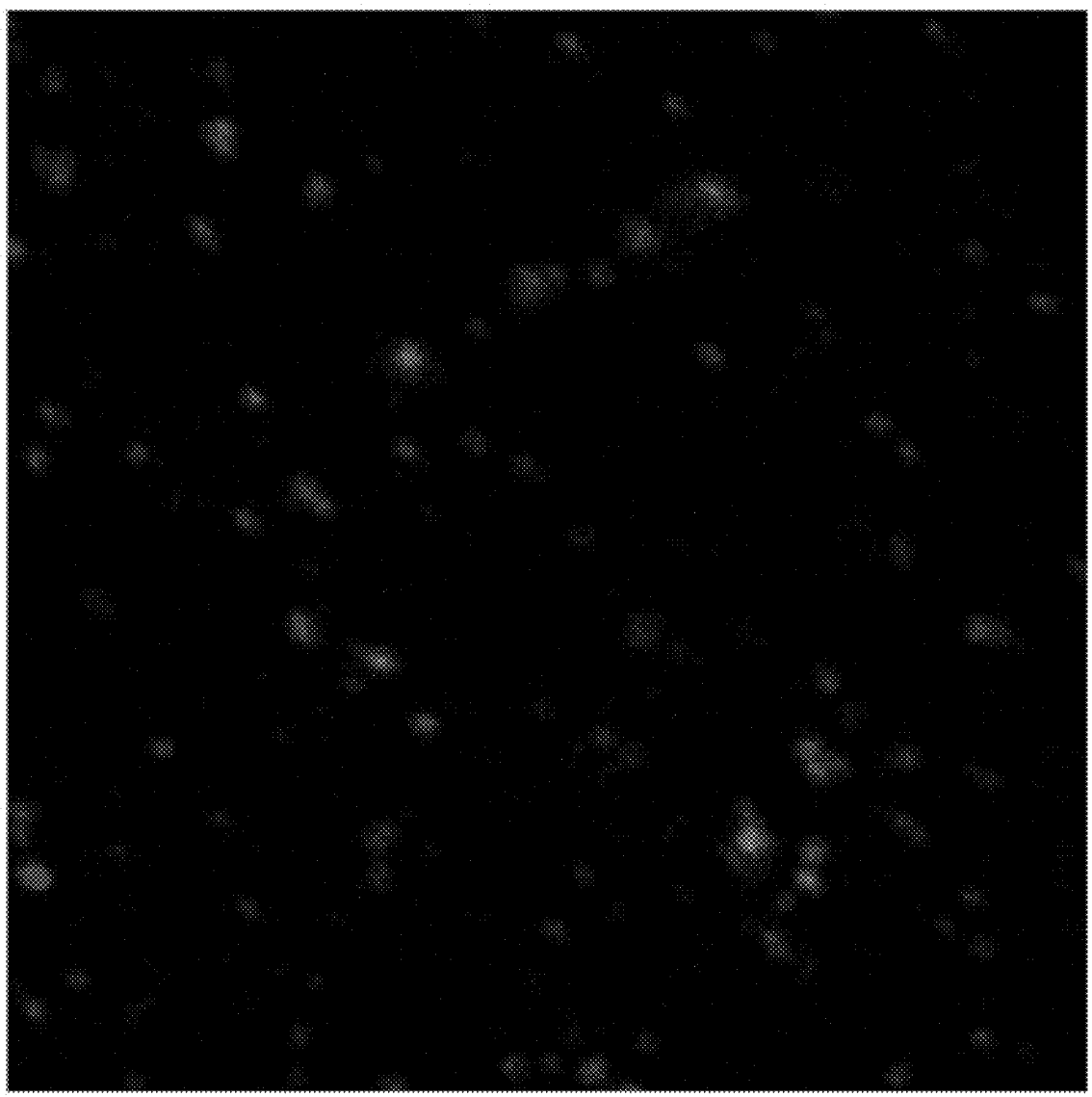

FIG. 4 demonstrates that VSV does not infect normal muscle cells. Cells were isolated from embryos of a transgenic C. elegans strain which expresses GFP in C. elegans muscle cells. Cells were infected with VSV recombinant virus which expressed the dsRED variant of GFP. The green fluorescent cells represent muscle cells and the fluorescent cells represent VSV infected cells.

Figure 5:
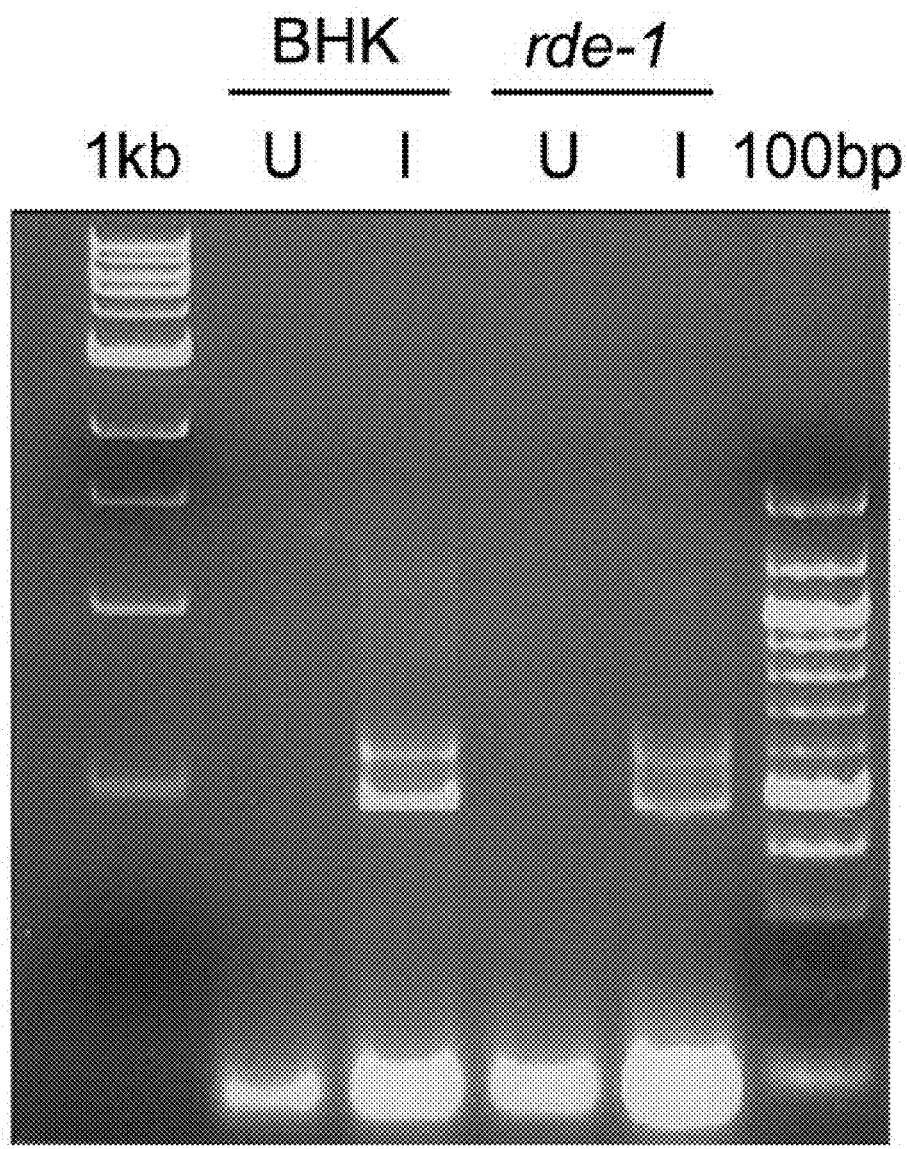

FIG. 5 demonstrates that VSV infected C. elegans can synthesize mRNAs that encode the viral N protein sequence. RNA was isolated from virus infected C. elegans and baby hamster kidney (BHK) cells. Infected and uninfected BHK cells were used as positive and negative assay controls, respectively. cDNA synthesis was made using oligonucleotide primers that specifically hybridized with the N protein mRNA transcripts and not to the viral RNA genome. The resultant cDNA sequences were amplified by PCR using oligonucleotide primers specific for N protein gene sequences. PCR signals were observed only in the infected C. elegans and BHK cells.

Figure 6A:
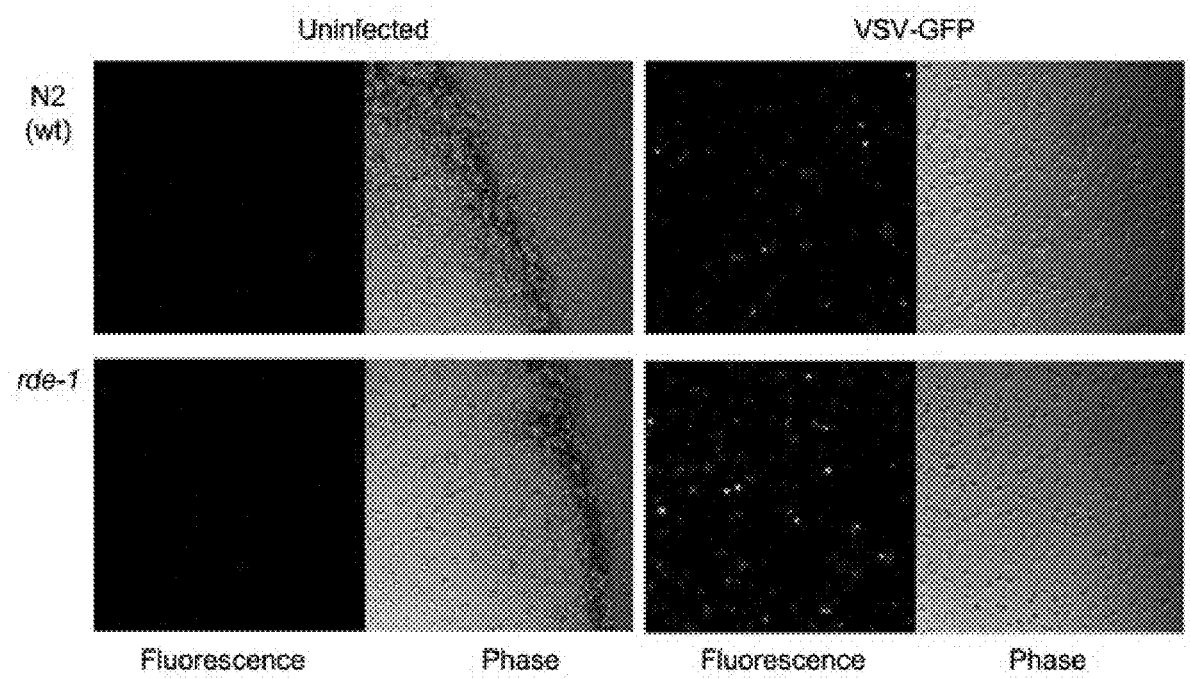

FIG. 6(a) demonstrates that cells isolated from a mutant C. elegans strain rde-1 that contains a defective gene in the RNA interference (RNAI) pathway can be infected with VSV.

Figure 6B:
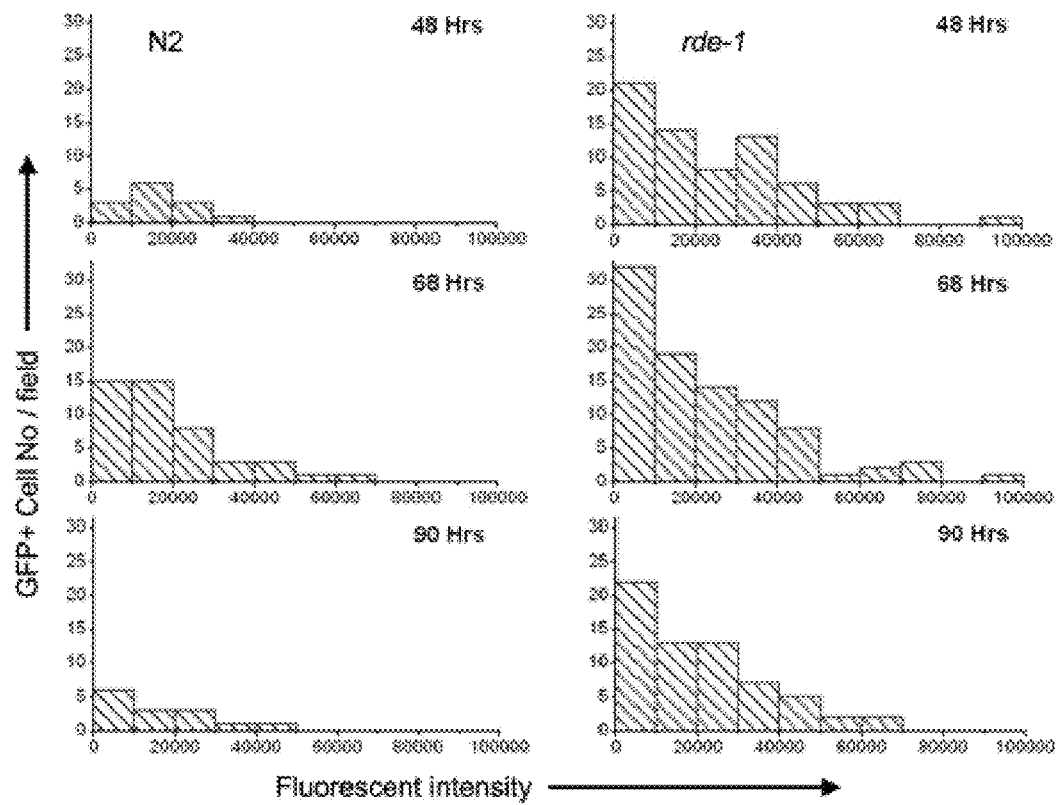

FIG. 6(b) demonstrates that the mutant C. elegans strain rde-1 is more susceptible to VSV infection than an unmutated wild-type C. elegans strain.

6. DETAILED OF THE INVENTION

This section presents a detailed description of the invention and its applications. This description is by way of several exemplary illustrations, in increasing detail and specificity, of the general methods of this invention. These examples are non-limiting and related variants will be apparent to one of skill in the art.

The present inventors demonstrated that disease phenomenon can be generated in C. elegans upon exposure to an animal virus. Therefore, the present invention provides an animal model for studying disease mechanisms comprising C. elegans infected with an animal virus. C. elegans of this invention may be wild-type or variants of C. elegans include transgenic or mutant C. elegans. In one embodiment, the C. elegans of the present animal model is the wild-type C. elegans. In another embodiment, the C. elegans of the present animal model is a transgenic C. elegans. Transgenic C. elegans have foreign genes incorporated into the C. elegans genome. The foreign genes may include but are not limited to human genes, mammalian genes or reporter genes. Transgenic C. elegans which are expressing reporter genes are constructed such that the reporter gen is expressed only under certain conditions. Mutant C. elegans have mutant C. elegans genes. The term "transgene" is used herein to describe genetic material that has been or is about to be artificially inserted into the host cell, particularly a cell of a living animal. The transgene is used to alter cells such that a permanent or transient genetic change is induced in a cell following incorporation of exogenous DNA. A permanent genetic change is generally achieved by introduction of the foreign DNA into the genome of the cell.

Studies using the present invention revealed that C. elegans rde-1 mutants defective in the RNA interference (RNAi) pathway are more susceptible to VSV infection than the wild-type C. elegans (see FIGS. 6a/b). Therefore, in another embodiment of the present invention, the C. elegans of the present animal model is a mutant C. elegan.

The present invention also provides an in vitro infection system comprising of C. elegans cells which have been isolated from C. elegans hosts and grown in culture which are infected with an animal virus.

Until the present invention, no reports have shown that a mammalian virus can infect C. elegans. Any potential virus would have to be able to replicate at temperatures used for nematode culture (25° C.), utilize cellular receptors and machinery sufficiently conserved in invertebrates, and have an infection cycle acute enough to cause disease in the short generation time of the host. The obligate intracellular lifestyles of viruses make them highly dependent on the host cell. Because of this, many viruses have very specific cellular tropism and narrow host ranges. The present invention provides an animal model for studying disease mechanism comprising C. elegans infected with obligate intracellular bacteria pathogens. In one embodiment, the bacterial pathogens are selected from a group of Chlamydia, rickettsia and ehrlichia. The present invention further provides an animal model for studying disease infection comprising C. elegans infected with obligate intracellular parasites. In particular, the parasites are selected from a group consisting of toxoplasma and malaria. Moreover, the obligate intracellular bacteria require the eukaryotic host to grow whereas the facultative bacteria, like the Pseudomonas can be propagated by other growth conditions without the eukaryotic cells. Therefore, the present invention also provides an animal model for studying disease infection comprising C. elegans infected with obligate intracellular pathogens including fungi and mold.

The present invention demonstrated that C. elegans infected with Vesicular stomatitis virus (VSV) revealed decrease in progeny and skewed development (see FIG. 1). Therefore, the present invention provides an animal model for studying disease mechanism comprising C. elegans that are infected with VSV or its variants. Vesicular stomatitis virus variants include recombinant VSV or mutant VSV. A recombinant VSV may contain a reporter gene. Various reporter genes will be apparent to one skilled in the art.

The vesicular stomatitis virus envelope protein known as VSV G protein is he protein on the VSV vireo which binds to a reporter on the cell surface to initiate infection. The viral envelope protein participates in virus binding to and/or entry of he infectious virus into a target cell. The term "viral envelop protein" refers to the protein(s) embedded in the membrane which surrounds the viral nucleocapsid. Viruses must encode viral proteins which recognize receptors on the host cell to initiate infection. Therefore, the envelop protein of other unrelated viruses can be incorporated into the membrane of VSV particles to replace the VSV G proteins, thereby requiring infection to be initiated by the envelop protein recognizing specific receptor on the cell surface.

In one embodiment, the present invention provides an animal model for studying disease mechanism comprising C. elegans infected with VSV wherein the G protein of the VSV is replaced with the envelop protein of another virus. The G protein of VSV can be replaced with the "envelop" proteins of other viruses such as Ebola, Hepatitis C or HIV. In another embodiment, the animal model comprises C. elegans infected with VSV wherein the VSV G protein has been incorporated into the virion membrane of a virus other than VSV.

The present invention provides a method for studying disease mechanism comprising C. elegans infected with chimeric recombinant viruses characterized by expression of virus particles containing VSV G protein in the viral membrane and viral genome containing non-VSV genomic sequence within the particle. The VSV G protein can be transiently incorporated into the virion membrane of other unrelated viruses by a strategy known as "pseudotyping". This strategy is useful for studying the replication of viruses for which cell lines are not available. Successful replication of the non-VSV viral genomes in C. elegans after introduction via VSV pseudotyping, again provides a strategy for screening anti-vials or therapeutic targets when standard cell culture systems are not available. The VSV G can be continually incorporated into the virion membrane for each round of cells infected by constructing a recombinant virus genome containing the VSV G protein envelop gene sequence. The chimeric viruses generated by either pseudotyping or recombinant methods can be used to study different aspects of the viral replication cycle for virus entry into cells or for effecting disease development in the animal. Knowledge of host genes that effect viral infection or disease development is important to identify potential physiological responses and/or pathways that are affected upon viral infection. These host genes and physiological pathways are also important targets for antivirals agents and vaccines.

In another embodiment, the animal model system comprises mutant C. elegans infected with chimeric virus pseudotypes characterized by expression of virus particles containing VSV G protein in the viral membrane and viral genome containing non-VSV genome sequences within the particle.

The present invention provides a method for studying disease conditions comprising infecting C. elegans with an animal virus and detecting a phenotype in the infected C. elegans. The phenotype of disease conditions include but are not limited to altered numbers of progeny or brood sizes, alteration in larval development or adult life span, muscle abnormalities leading to uncoordinated movements or egg-laying defects, altered responses to environmental stimuli such as temperature and odorants. The presence of any of these phenotypes or combinations of phenotype is indicative of disease conditions. One skilled in the art can implore many biological and biochemical techniques such as immunochemistry, differential interference contrast and fluorescence microscopy to examine the physiological changes of the C. elegans.

The present invention also provides a method for studying disease conditions comprising infecting C. elgans with VSV; and detecting a change in phenotype of the infected C. elegans wherein change in phenotype is indicative of disease conditions. VSV may be wild-type, mutant or transgenic variants.

VSV G infected C. elegans infection grown in liquid media at 25° C. for 24 hours displayed disease phenotypes including decreased numbers of progeny, defects in larval development, muscle abnormalities leading to uncoordinated movement or egg-laying defects and death. Therefore, in one embodiment, the change in phenotype includes decreased numbers of progeny, alteration in larval development or adult life-span, muscle abnormalities leading to uncoordinated movement or egg-laying defects and death.

The present invention provides a method for identifying host genes that are important for viral infection. In one embodiment, transgenic C. elegans containing a mammalian gene is used to identify a foreign host protein that is important for virus replication. In particular, the present invention provides a method for identifying genes important for development of disease conditions comprising infecting a C. elegans with an animal virus; and detecting a change in phenotype of the infected C. elegans wherein an increase in a phenomenon associated with viral disease mechanism is indicative of disease conditions; and identifying genes that are either induced or repressed by infection of the C. elegans. Once these genes have identified, then their mammalian counterparts can be tested to see whether the mammalian host genes are important for viral replication or disease production.

The present invention can sued to study aspects of innate immunity that affect the ability of the host to combat viral infection. Standard mutagenesis protocols can be used to isolate and characterize mutant strains of C. elegans that are more susceptible or resistant to VSV infection. Random mutagenesis will allow for large-scale screens of the C. elegans genome to select for those host mutants that appear to develop more or less several disease phenotypes. Many of the C. elegans mutations may be in the host factors or pathways utilized by the virus during the infectious cycle. Gene mutations that contribute to the defense mechanisms including the innate immune system may be identified from this screen. The mutant screen may identify new genes or new functions for previously known genes.

Replacement of the VSV G protein with other viral envelop protein (Hepatitis C, Ebola, West Nile Virus) means that infection is dependent on the ability of the new envelop protein to bind a receptor to initiate infection. Once the viral genome is in the cell relevant envelop protein recognized its receptor on the C. elegans. Replacement of the VSV genome with other viral genomes allows identification of the host genes which are important for the replication of he viral genome of interest. Therefore, the present invention provides a method for identifying genes important for development of disease conditions wherein the animal virus is VSV. In particular, the present invention provides a method identifying genes important for development of disease conditions comprising infecting a C. elegans with vesicular stomatitis virus; and detecting a change in phenotype of the infected C. elegans wherein an increase in a phenomenon associated with viral disease mechanism is indicative of disease conditions; and identifying genes that are either induced or repressed by infection of the C. elegans. The phenomenon associated with viral disease mechanism includes decreases numbers of progeny, defects in larval development, alteration in adult lifespan, muscle abnormalities leading to uncoordinated movement or egg-laying defects and death.

In many instances, the limiting step for studying viral pathogenesis is the ability to identify host genes that are important for the disease process. A major barrier to host infection by a virus is the requirement for the expression of specific receptors on the host cell surface which are recognized by a virus to initiate entry into the cell. Therefore, identification of the host gene(s) which encode the receptor for a virus is an important determinant of the infection process. The present invention provides a method for identifying genes important for development of disease conditions by infecting a mutant C. elegans with an animal virus; detecting a change in phenotype of thee infected C. elegans wherein an increase in a phenomenon associated with viral disease mechanism is indicative of disease conditions; and identifying genes that are either induced or repressed by infection of the C. elegans.

Recombinant or chimeric viruses can be used to screen for antivirals such as but not limited to inhibitors of the fusion function of the envelop protein or receptor blocker's which could prevent infection. Other non-VSV proteins can be expressed in the background of the VSV recombinant viruses to identify the cognate interaction host factors as well as evaluate their potential effects on disease development. In one embodiment, the non-VSV viral proteins are apoptosis mediators. In yet another embodiment, the non-VSV viral proteins are protease inhibitors.

The C. elegans host may comprise alterations to endogenous genes. The host animal may be "knockouts" for a target gene comprising a partial or complete loss of function in one or all alleles of an endogenous gene of interest. In a knockout, the target expression is undetectable or insignificant. For example, a knockout of a receptor protein gene means the expression of the receptor protein is not detectable and function of the receptor protein is ablated.

Another limiting step for studying viral replication is the availability of suitable cell lines or animals. Suitable cell lines or animals can be obtained by generating transgenic C. elegans strains which express foreign proteins necessary for virus infection. This may be in combination with a knockout of the C. elegans endogenous gene, while introducing an exogenous foreign gene, while introducing an exogenous foreign gene. The present invention further provides a strategy for generating an animal host model for viruses which cannot be easily grown or studied in cell culture by constructing multi-transgenic C. elegans which express a combination of important host determinants (receptor and intracellular host factors). For example, if a virus does not infect C. elegans, because the nematode does not express an appropriate receptor, genes from a susceptible host such as a mouse could be screened in C. elegans to identify receptors.

Potential therapeutics that target disease symptom pathways may interfere with disease development while not significantly effecting viral replication. Therefore, another embodiment of the present invention provides a method for screening agents that effect viral diseases comprising combining an agent with transgenic C. elegans wherein the transgenic C. elegans are characterized by expression of a transgenic nucleotide sequence encoding a VSV G protein and determining the effect of the agent in the transgenic C. elegans on a phenomenon associated with viral disease mechanism. The present invention provides therapeutic agents produced using the present method of screening for agents for effect on viral disease comprising infecting C. elegans with an animal virus; combing an agent with the infected C. elegans; and determining the effect of the agent on a phenomenon associated.

In another embodiment, the present method of screening for agents for effect on viral diseases comprising infecting C. elegans with VSV; combining an agent with the infected C. elegans; and determining the effect of the agent on a phenomenon associated with viral disease mechanism wherein the expression of the reporter protein is decreased.

In yet another embodiment, the present invention provides a method for testing an agent for effectiveness against a disease condition comprising obtaining a C. elegans infected with an animal virus wherein the C. elegans exhibits a disease condition phenotype; delivering the agent to the C. elegans; and analyzing the effectiveness of the agent on the C. elegans wherein an agent that diminishes the phenotype is indicative of an agent that has effectiveness against the disease condition. The phenotype is selected from the group consisting of decreased of number of progeny defects in larval development, alteration in adult life-span, muscle abnormalities leading to uncoordinated movement or egg-laying defects and death. The present invention also provides therapeutic agents produced using the present method of testing an agent for effectiveness against a disease condition.

The G protein of VSV can be replaced with the "envelope" proteins of other viruses such as Ebola o HIV. This provides a method for identifying the host receptor for viruses which either do not grow well or present unusual growth or biohazard containment issues. These recombinant viruses can be used to screen for antivirals which as inhibitors of he function of the envelope protein or "receptor blockers" which could prevent infection. Other non-VSV viral proteins can be expressed in the background of the VSV recombinant viruses to identify the cognate interacting host factors aw swell as evaluate their potential effects on disease development. In one embodiment, non-VSV viral proteins are selected from the group consisting of serpin and apoptosis mediators.

The present invention can also be used to study the infection mechanism and defense mechanisms of mutant strains. These mutant strains contain mutations in genes including the defensin-like antimicrobial peptides, Toll-signaling receptors, RNA interference mechanisms, apoptisis regulators and MAPK-signaling cascades. Infection of the C. elegans mutants can be characterized to specifically determine the relative contributions of different innate immune system components to viral disease and to identify how VSV infection is altered in these hosts. For example, if a mutant is infected with such as the defensin-like antimicrobial peptides, one of several outcomes can be envisioned. If a gene is not involved in disease development or protection, then the result should look identical to that seen in the wild-type or normal C. elegans. However, if the gene is involved in disease development, then the disease symptoms should not appear or will be less severe in the infected mutant (which is defective in this gene) than in the wild-type or normal C. elegans. If the gene is involved in disease protection such as immunity, then the disease symptoms should be more severe in the infected mutant than tin the wild-type or normal C. elegans. In the present invention, infection by rde-1 mutant led to more cells being infected and VSV gene expression as detected by the intensity of green fluorescent protein expression in each cell was higher than in the infected normal C. elegans (see FIG. 6a/b).

7. EXAMPLES

The following examples are given for the purpose of illustrating various embodiments of the invention and are not meant to limit the present invention.

7.1 C. elegans Infection Using Different Viruses

C. elegans were infected with VSV, vaccinia virus, catfish channel virus (CCV), and baculovirus. Vaccinia is a poxvirus. CCV is a herpes virus capable of replication at 25° C. Baculoviruses are insect viruses that are capable of replicating in other invertebrate hosts.

The infections grown in liquid media at 25° C. for 24 hours were examined for disease phenotypes including decreased numbers of progeny, alteration in larval development or adult life-span, muscle abnormalities leading to uncoordinated movement or egg-laying defects and death.

7.2 C elegans Infections Using Infected HeLa Cell Monolayers

Disease phenotypes were observed in C. elegans that fed on VSV-infected HeLa cells where the infected monolayers grown in Dulbecco Modification of Eagle Medium (DMEM) supplemented with 5% fetal calf serum provided a source of virons to infect C. elegans. Cells were infected with VSV at a multiplicity of 0.1 to 0.3 infectious virus particles per cell overnight at 37° C. Wild-type strain C. elegans larvae at the L4 stage were added directly to the media and maintained at 25° C. Negative controls were uninfected HeLa cells.

After seven days, infected samples demonstrated a decrease in the number of nematodes between 50% and 70% of the uninfected controls.

7.3 VSV Infection s by VSV in Worm Growth Media

C. elegans cultured in worm growth (WG) media (10 mM NaCl, 10 mM $KH_2PO_4$; pH 6.0; 10 mM Potassium citrate; 1× trace metals; 3 mM $Cal_2$; 3 mM $MgSO_4$; 13 µM cholesterol) were exposed to VSV in a cell-free supernatant.

OP50, an auxotrophic strain of Escherichia coli deficient in uracil production was used as a food source for C. elegans. HEPES buffer (10 mM, pH 7.0) was added to all samples to maintain a constant pH. VSV stocks were purified and resuspended in phosphate buffered saline (PBS) to remove cell serum and cellular debris.

Stage L3 larvae were added to individual wells of 12-well plates. Each well contained 750 µl of media supplemented with one-tenth total volume of an overnight OP50 culture in LB and $10^6$ PFU/ml VSV or an equal volume of PBS. After three days at 25° C., the resulting populations were counted and progeny were scored by developmental stage. All progeny were in the F1 generation.

The overall population size was significantly reduced in the presence of VSV and the developmental stages of progeny were skewed toward the early larval stages (see FIG. 1). Since there were no infected HeLa cells present, disease was due to the presence of VSV. E. coli OP50 present in the wells, were alive and residual uracil in the LB media allowed for some bacterial growth but the same results described in FIG. 1 were observed when heat-activated bacteria were used as food source.

7.4 UV-inactivated VSV

A series of infections using UV-inactivated VSV were performed to determine whether the observed disease phenotype required the presence of infectious virus or was due to toxicity of viral proteins. One set of nematodes was exposed to $10^6$ PFU/mL equivalent doses of UV-inactivated VSV. Contrary to infectious VSV, the presence of UV-inactivated VSV had no effect on the total population size after three days of exposure (see FIG. 2). The developmental stage was skewed compared to uninfected samples but to a much lower degree than in samples containing infectious virus.

7.5 Assays for Viral Infection and Replication

7.5.1 Confocal Microscopy

A gene encoding green fluorescent protein (GFP) or its red derivative (dsRED) has been utilized as a marker for gene expression in prokaryotic and eukaryotic cells. GFP expressed in a heterologous prokaryotic or eukaryotic host produces a protein capable of fluorescence. C. elegans was infected with a recombinant strain of VSV that carried GFP or dsRED in the viral genome. The presence of GFP indicated transcription of the viral RNA and expression of virus-encoded proteins because GFP is not a virus structural protein and is not packaged in the VSV virion. Morphologic changes of nematodes exposed to VSV included an increase in fluorescence of the intestinal lysosomes and separations o the intestinal lumen from the outer cuticle layers in nematodes exposed to VSV.

7.5.2 Antibody Staining

Antibodies generated against vesicular stomatits virus G protein (VSV G protein); N and M proteins were utilizes to detect for the production of viral protein in infected C. elegans. The infected C. elegans cells were fixed with 4% paraformaldehyde incubated with an antibody against VSV protein and secondary antibody then examined by fluorescent microscopy.

7.5.3 RNA Analysis

RNA was isolated from virus infected C. elegans and baby hamster kidney cells (BHK) cell. Infected and uninfected BHK cells were used as positive and negative assay controls, respectively. cDNA synthesis was made using oligonucleotide primers that specifically hybridized with N protein mRNA transcripts at the 3' terminus and to the viral RNA genome. The resultant cDNA sequences were amplified by Polymerase Chain Reaction (PCR) using oligonucleotide primers specific for N protein gene sequences. PCR signals were observed only in the infected C. elegans and BHK cells (see FIG. 5).

7.6 VSV Infection of C. elegans Cells in Culture

Cells were isolated from C. elegans embryos and grown n culture in Leibovitz's L-15 media supplemented with 5% fetal calf serum at 25° C. Recombinant VSV expressing GFP was added to the media. The cells were incubated with the recombinant virus for 12 hours at 25° C. at a multiplicity of 10 infectious units per cell. At 48 hour post-infection the cells were examined by fluorescent microscopy for GFP expression (see FIG. 3).

7.7 VSV Infection of Transgenic C. elegans Cells in Culture

Cells were isolated from transgenic C. elegans (strain PD4251) embryos as in Section 7.6. C. elegans strain PD4251 is a transgenic nematode line that has GFP incorporated into the *C. elegans* genome an under the regulation of the myo-3 promoter. Thus, GFP expression is observed only in cells which activate the myo-3 promoter, including the body wall muscle cells. Recombinant VSV expressing the dsRED form of GFP was added to the media and the cells were examiner 48-96 hours post-infection by fluorescent microscopy. The detection of GFP fluorescence was used to identify muscle cells and dsRED fluorescence detection to identify infected cells.

Both green and red fluorescence was detected in the cell culture. However, the fluorescent signals did not co-localize (see FIG. 4). A yellow signal would represent the presence of GFP from the muscle cell and dsRED protein for VSV infection in the same cells. This demonstrates that under these conditions the VSV is not infecting muscle cells but infecting other cell types in the *C. elegans.*

7.8 VSV Infection of Mutant *C. elegans* Cells in Culture

Cells were isolated from mutant (strain WM27) and wild type *C. elegans* embryos as in Section 7.6. *C. elegans* strain WM27 carries the mutant rde-1 (ne219) allele which results in Rde-1 deficiency. Rde-1 is required in the RNA interference pathway and *C. elegans* strain WM27 is defective in the RNA interference pathway. Recombinant VSV expressing GFP was added to the media and the cells were examined 48-96 hours post-infection by fluorescent microscopy to detect GFP fluorescence.

GFP fluorescence was observed in a greater number of rde-1 mutant cells than wild type cells and the fluorescent intensities were higher in the rde-1 mutant cells (see FIG. 6*a/b*). This suggests that the rde-1 strain is more susceptible to VSV infection than the wild type *C. elegans* strain.

All references cited herein are incorporated herein by references in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

REFERENCES

Epstein, H. E., and Shakes, D. C. (eds). Methods in Cell Biology, Volume 48*, Caenorhabditis elegans*: Modern Biological Analysis of an Organism. Academic Press, San Diego, 1985.

Garsin, D. A., Sifri, C. D., Mylonakis, E., Qin, X., Singh, K. V., Murray, B. E., Calderwood, S. B., and Ausubel, F. M. (2001). A simple model host for identifying Gram-positive virulence factors. Proc. Natl. Acad. Sci. USA. 98: 10872-7.

Kim, D. H., Feinbaum, R., Alloing, G., Emerson, F. E., Garsin, D. A., Inoue, H., Tanaka-Hino, M., Hisamoto, N., Matsumoto, K., Tan, M. W., and Ausuel, F. M. (2002). A conserved p38 MAP kinase pathway in *Caenorhabditis elegans* innate immunity. Science. 297: 623-6.

Labrousse, A., Chauvet, S., Couillault, C., Kurz, C. L., and Ewbank, J. J. (2000). *Caenorhabditis elegans* is a model host for *Salmonella typhiurium*. Current Biology. 10: 1543-45.

Mahajan-Miklos, S., Tan, M. W., Rahme, L. G., and Ausubel, F. M. (1999). Molecular Mechanisms of bacterial virulence elucidated using a *Pseudomonas aeruginosa-Caenorhabditis elegans* pathogenesis model. Cell. 96: 47-56.

Pujol, N., Link, E. M., Liu, L. X., Kurz, C. L., Alloing, G., Tan, M. W., Ray, K. P., Solari, R., Johnson, C. D., and Ewbank, J. J. (2001). A reverse genetic analysis of components of the Toll signaling pathway in *Caenorhabditis elegans*. Current Biology. 111: 809-21.

Tan, M. W., Rahme, L. G., Stemberg, J. A., Tompkins R. G., and Ausubel, F. M. (1999). *Pseudomonas aeruginosa* killing of *Caenorhabditis elegans* used to identify *P. aeruginosa* virulence factors. Proc. Natl. Acad. Sci. USA. 96: 2408-13.

The invention claimed is:

1. An animal model for studying disease mechanisms comprising *C. elegans* infected with an animal virus wherein a change in phenotype of the infected *C. elegans* not detected in an uninfected *C. elegans* is indicative of disease conditions in the infected *C. elegans.*

2. An animal model for studying disease mechanisms comprising *C. elegans* infected with vesicular stomatitis virus wherein a change in phenotype of the infected *C. elegans* not detected in an uninfected *C. elegans* is indicative of disease conditions in the infected *C. elegans.*

3. The animal of claim 2, wherein the G protein of the vesicular stomatitis virus is replaced with an envelope protein of a virus other than VSV.

4. The animal model of claim 3, wherein the G protein of the vesicular stomatitis virus is replaced with an envelope protein of Ebola or Hepatitis C virus.

5. The animal model of claim 1, wherein the *C. elegans* is selected from the group consisting of wild-type, mutant and transgenic *C. elegans.*

6. The animal model of claim 2 wherein the *C. elegans* is selected from the group consisting of wild-type, mutant and transgenic *C. elegans.*

* * * * *